(12) United States Patent
Alfonso et al.

(10) Patent No.: US 8,853,371 B2
(45) Date of Patent: Oct. 7, 2014

(54) PROCESS FOR PREPARING UNAGGREGATED ANTIBODY FC DOMAINS

(75) Inventors: Pedro Alfonso, Malvern, PA (US); Michael Capaldi, Malvern, PA (US); Dennis Dong, Berwyn, PA (US); Thomas R. Gervais, Malvern, PA (US); Joshua Goldstein, Malvern, PA (US); Allen B. Magill, Malvern, PA (US); Nicole Quinlan, Malvern, PA (US); Deepak Saini, Malvern, PA (US)

(73) Assignee: Janssen Biotech, Inc., Horsham, PA (US)

( * ) Notice: Subject to any disclaimer, the term of this patent is extended or adjusted under 35 U.S.C. 154(b) by 1241 days.

(21) Appl. No.: 11/875,243

(22) Filed: Oct. 19, 2007

(65) Prior Publication Data

US 2009/0171072 A1 Jul. 2, 2009

Related U.S. Application Data

(60) Provisional application No. 60/862,110, filed on Oct. 19, 2006.

(51) Int. Cl.
| | | |
|---|---|---|
| *C07K 17/00* | (2006.01) | |
| *B01D 15/38* | (2006.01) | |
| *C07K 1/22* | (2006.01) | |
| *A61K 39/395* | (2006.01) | |

(52) U.S. Cl.
CPC ...... *A61K 39/39591* (2013.01); *B01D 15/3809* (2013.01); *C07K 1/22* (2013.01); *C07K 2317/52* (2013.01); *C07K 2319/30* (2013.01)
USPC .......................................... 530/413; 530/412

(58) Field of Classification Search
None
See application file for complete search history.

(56) References Cited

U.S. PATENT DOCUMENTS

| 6,127,526 A | 10/2000 | Blank |
| 6,870,034 B2 | 3/2005 | Breece et al. |
| 7,393,662 B2 * | 7/2008 | Heavner et al. .............. 435/69.7 |
| 2005/0226864 A1 * | 10/2005 | Hinton et al. .............. 424/133.1 |
| 2008/0064860 A1 | 3/2008 | Sun et al. |

FOREIGN PATENT DOCUMENTS

| EP | 1 568 710 B1 | 8/2005 |
| WO | WO 01/72769 A2 | 10/2001 |
| WO | WO 02/098531 A1 | 12/2002 |
| WO | WO 2008/025747 A1 | 3/2008 |
| WO | WO 2009/017941 A1 | 2/2009 |

OTHER PUBLICATIONS

HiTrap TM product information sheet (2005, p. 1-8).*
Webster's II New Riverside University Dictionary (1988, p. 1033).*
Antibody Purification Handbook (Amersham Biosciences, 2002, p. 1-110.*
Martin, et al., "A New Form of Chromatogram Employing Two Liquid Phases," The Journal of Biochemistry, 35: 1358-1368 (1941).
Ishihara, et al., "Rational methods for predicting human monoclonal antibodies retention in protein A affinity chromatography and cation exchange chromatography Structure-based chromatography design for monoclonal antibodies," Journal of Chromatography A, 1093: 126-138 (2005).
Yigzaw, et al., "Exploitation of the Adsorptive Properties of Depth Filters for Host Cell Protein Removal during Monoclonal Antibody Purification," Biotechnol. Prog., 22: 288-296 (2006).
PCT International Search Report dated Jul. 30, 2008.

* cited by examiner

*Primary Examiner* — Yunsoo Kim
(74) *Attorney, Agent, or Firm* — Kirk Baumeister

(57) ABSTRACT

Methods useful for producing a solution of purified Fc peptide chains are disclosed. The methods employ protein A chromatography to separate high molecular weight, aggregated peptide chains comprising antibody Fc domains from lower molecular weight unaggregated peptide chains that also comprise antibody Fc domains. The solutions of purified Fc peptide chains obtained by the methods of the invention contain less than 5% aggregate and greater than 70% of the Fc peptide chains subjected to purification.

8 Claims, 4 Drawing Sheets

PROCESS FOR PREPARING UNAGGREGATED ANTIBODY FC DOMAINS

CROSS-REFERENCE TO RELATED APPLICATIONS

This application claims the benefit of U.S. Provisional Application Ser. No. 60/862,110, filed 19 Oct. 2006, the entire contents of which is incorporated herein by reference.

FIELD OF THE INVENTION

This invention relates to the use of protein A chromatography to separate aggregated and unaggregated peptide chains comprising antibody Fc domains.

BACKGROUND OF THE INVENTION

The use of monoclonal antibody (mAb) molecules that comprise Fc peptide chains as therapeutic reagents has become an effective approach for the treatment of various diseases. Antibody-derived molecules that contain Fc peptide chains, such as mimetibody molecules, described infra, and Fc fusion molecules, also have therapeutic potential. In addition, these molecules are useful research tools for gaining a better understanding of the immunopathogenesis of various diseases as well as other biological processes.

Large-scale production and purification of antibody, mimetibody, and Fc fusion molecules is necessary to prepare these Fc peptide chain molecules for therapeutic or research use. A commonly encountered problem in the production and purification of such molecules is the formation of soluble high molecular weight aggregates comprising multiple Fc peptide chain molecules (e.g., aggregates of more than two unaggregated, low molecular weight antibody or mimetibody molecules). The presence of such aggregates is highly undesirable in therapeutic preparations, because of the risk that some patients will suffer life-threatening immune reactions in response to receiving aggregate. Additionally, Fc peptide chain aggregates can cause the formation of undesirable insoluble precipitates in Fc peptide chain preparations intended for research or therapeutic uses.

One goal during the purification of Fc peptide chain molecules is to obtain an unaggregated Fc peptide chain product (e.g. unaggregated, low molecular weight antibody or mimetibody molecules) in high yield that is essentially free of aggregated molecules. Typically, a preparation of purified Fc peptide chains containing less than 5% aggregate at a total percent yield of Fc peptide chains greater than 70% is desired.

One of the first steps in the production and purification of Fc peptide chain molecules is normally a protein A chromatography resin based purification step. Protein A chromatography resins comprise protein A peptide chains that specifically bind Fc peptide chains. This binding activity does not discriminate between aggregated or unaggregated Fc peptide chains—both are bound to protein A chromatography resins. Importantly, protein A chromatography resins separate Fc peptide chains from other molecules on the basis of this specific binding. Such resins do not separate Fc peptide chains from other molecules or complexes on the basis of molecular weight differences. Consequently, in conventional protein A chromatography methods both aggregated, high molecular weight Fc peptide chains and unaggregated, low molecular weight Fc peptide chains are released from the protein A chromatography resin during an elution step. This produces an aqueous solution comprising large quantities of both undesirable, aggregated Fc peptide chain molecules and desirable, unaggregated Fc peptide chain molecules.

One consequence of the inability of conventional protein A chromatography methods to separate aggregated and unaggregated Fc peptide chain molecules is that several additional purification processes such as size exclusion chromatography or ion exchange chromatography techniques are needed to obtain preparations of unaggregated Fc peptide containing less than 5% aggregate. This subsequent processing is expensive, time consuming, and causes total percent yield values to decrease well below 70%.

Thus, a need exists for protein A chromatography-based purification methods that produce purified Fc peptide chain preparations containing less than 5% aggregate at total percent yield values greater than 70% without the use of additional purification processes.

SUMMARY OF THE INVENTION

Figure 1:
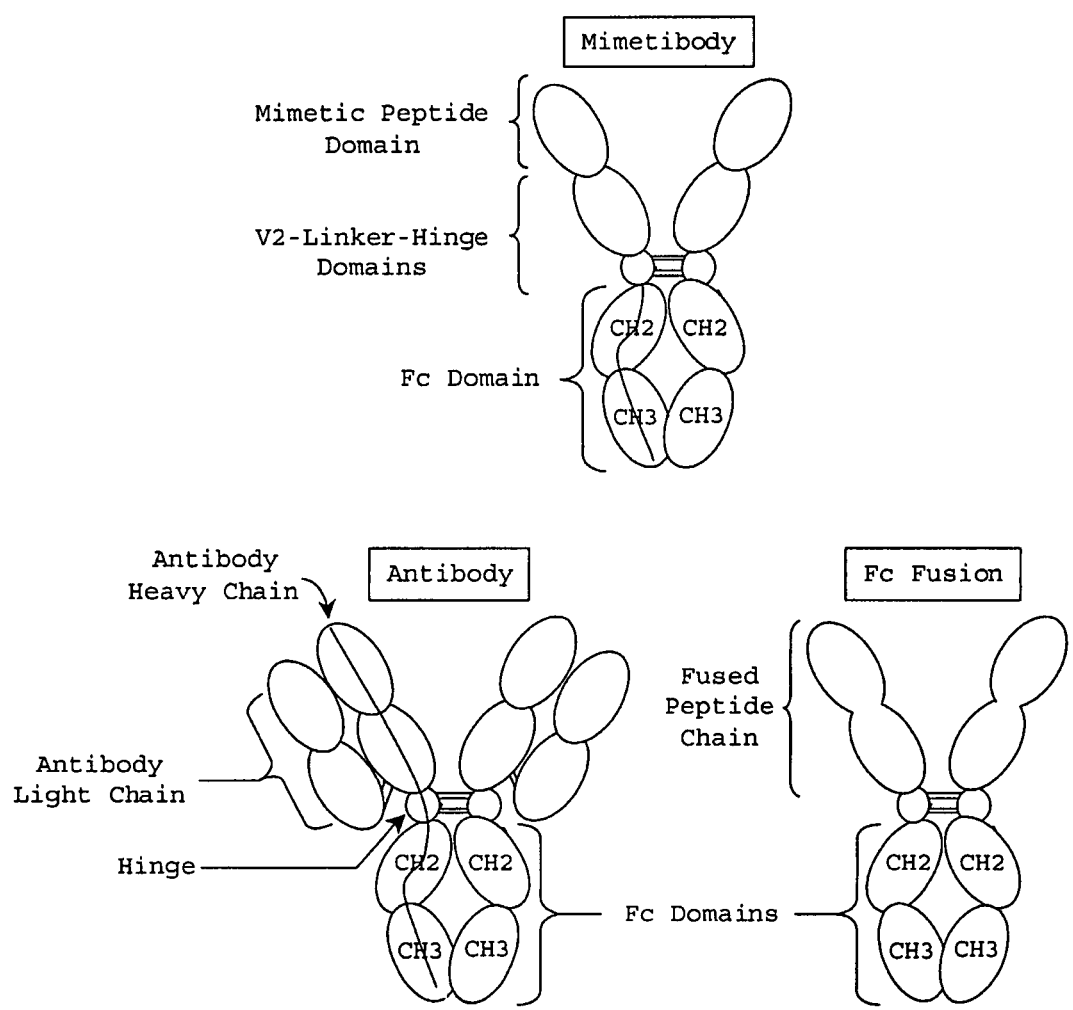
FIG. 1 Schematic of representative Fc peptide chain molecules. Selected peptide chain features are noted.

One aspect of the invention is a method for producing a solution of purified unaggregated Fc peptide chains comprising the steps of providing an aqueous sample comprising unaggregated Fc peptide chains and aggregated Fc peptide chains; contacting the sample with a population of protein A peptide chains bound to an insoluble material and capable of binding greater than 70% of the total mass of unaggregated Fc peptide chains and aggregated Fc peptide chains in the sample; contacting the population of protein A peptide chains with an aqueous solution having a salt concentration of 10 mM to 129 mM and a pH of 3.24 to 3.93; and removing the aqueous solution from contact with the population of protein A peptide chains to produce a solution of purified unaggregated Fc peptide chains comprising less then 5% aggregated Fc peptide chains; wherein the total percent yield of Fc peptide chains is greater than 70%.

Another aspect of the invention is a method for producing a solution of purified unaggregated Fc peptide chains comprising the steps of providing an aqueous sample comprising unaggregated Fc peptide chains and aggregated Fc peptide chains; contacting the sample with a population of protein A peptide chains bound to an insoluble material and capable of binding greater than 70% of the total mass of unaggregated Fc peptide chains and aggregated Fc peptide chains in the sample; contacting the population of protein A peptide chains with an aqueous solution having a salt concentration of 41 mM to 97 mM and a pH of 3.42 to 3.74; and removing the aqueous solution from contact with the population of protein A peptide chains to produce a solution of purified unaggregated Fc peptide chains comprising less then 5% aggregated Fc peptide chains; wherein the total percent yield of Fc peptide chains is greater than 70%.

Another aspect of the invention is a method for producing a solution of purified unaggregated Fc peptide chains comprising the steps of providing an aqueous sample comprising unaggregated Fc peptide chains and aggregated Fc peptide chains; contacting the sample with a population of protein A peptide chains bound to an insoluble material and capable of binding greater than 70% of the total mass of unaggregated Fc peptide chains and aggregated Fc peptide chains in the sample; contacting the population of protein A peptide chains with an aqueous solution having a salt concentration of 55 mM to 85 mM and a pH of 3.50 to 3.66; and removing the aqueous solution from contact with the population of protein A peptide chains to produce a solution of purified unaggregated Fc peptide chains comprising less then 5% aggregated Fc peptide chains; wherein the total percent yield of Fc peptide chains is greater than 70%.

Another aspect of the invention is a method for producing a solution of purified unaggregated mimetibody Fc peptide chains comprising the steps of providing an aqueous sample comprising unaggregated mimetibody Fc peptide chains and aggregated mimetibody Fc peptide chains; contacting the sample with a population of protein A peptide chains bound to an insoluble material and capable of binding greater than 70% of the total mass of unaggregated mimetibody Fc peptide chains and aggregated mimetibody Fc peptide chains in the sample; contacting the population of protein A peptide chains with an aqueous solution having a tris(hydroxymethyl)aminomethane acetate salt concentration of 55 mM to 85 mM and a pH of 3.50 to 3.66; and removing the aqueous solution from contact with the population of protein A peptide chains to produce a solution of purified unaggregated mimetibody Fc peptide chains comprising less then 5% aggregated mimetibody Fc peptide chains; wherein the total percent yield of mimetibody Fc peptide chains is greater than 70%.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the invention, exemplary compositions and methods are described herein.

The term "aggregate" means a molecule or complex comprising more than four individual Fc peptide chains depending on whether the additional Fc peptide chains are covalently or non-covalently bonded to the four Fc peptide chains. The aggregated form of a molecule or complex has a higher molecular weight than the unaggregated form.

The term "antibody" means immunoglobulin or antibody molecules comprising polyclonal antibodies, monoclonal antibodies including murine, human, humanized and chimeric monoclonal antibodies and antibody fragments, portions, or variants. Antibodies are secreted proteins constitutively expressed and secreted by plasma cells. Antibodies can also be produced using plasma cells immortalized by standard methods such as hybridoma generation or by transfection of antibody heavy and/or light chain genes into an immortalized B cell such as a myeloma cell or other cell types, such as Chinese hamster ovary (CHO) cells, plant cells and insect cells.

The term "Fc peptide chain" means a peptide chain comprising a portion of an immunoglobulin heavy chain $C_H2$ constant region peptide chain and immunoglobulin heavy chain $C_H3$ constant region peptide chains sufficient to bind protein A. Such constant region peptide chains may be derived from antibody heavy chains of any isotype, such as $IgG_1$, and may also be referred to as an "Fc domain" (see e.g. FIG. 1). An Fc peptide chain may be an individual peptide chain comprising both an immunoglobulin heavy chain $C_H2$ constant region peptide chain and an immunoglobulin heavy chain $C_H3$ constant region peptide chain sufficient to bind protein A (e.g. single chain antibody) or an association of two, three, four or more such individual peptide chains (e.g. association of antibody or mimetibody molecules). Fc peptide chains represent a genus of molecules that includes, for example, antibody molecules comprising Fc domains, Fc fusion peptide chains comprising Fc domains, and mimetibody peptide chains comprising Fc domains (FIG. 1). The term "Fc peptide chain" can be used to describe unaggregated Fc peptide chains, aggregated Fc peptide chains, or both aggregated and unaggregated Fc peptide chains.

The term "heavy chain" as used herein means the heavier, in terms of molecular weight, of the two types of polypeptide chains that are found in immunoglobulin and antibody molecules.

The term "mimetibody" means an peptide chain comprising the generic formula (I):

$$(\text{M-L-V2-H}\!\!-\!\!C_H2\text{-}C_H3)_{(t)} \qquad (\text{I})$$

where M is a bioactive peptide chain, L is a peptide chain linker, V2 is a portion of a C-terminus of an immunoglobulin variable region, H is a portion of an immunoglobulin variable hinge region peptide chain, $C_H2$ is an immunoglobulin heavy chain $C_H2$ constant region peptide chain and $C_H3$ is an immunoglobulin heavy chain $C_H3$ constant region peptide chain and t is an integer less than, or equal to, 4. The $C_H2\text{-}C_H3$ portion of a mimetibody comprises a portion of an antibody Fc domain and is an Fc peptide chain that can be bound by protein A. Mimetibody molecules are representatives of a genus of peptide chains comprising Fc domains. This genus of Fc peptide chains includes, for example, antibody molecules comprising Fc domains, Fc fusion peptide chains comprising Fc domains, and mimetibody peptide chains comprising Fc domains (FIG. 1).

The term "peptide chain" means a molecule that comprises at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The value "percent aggregate" is the percentage by mass of aggregated Fc peptide chain present in a sample relative to the total amount by mass of all Fc peptide chains, both aggregated and unaggregated, present in the sample. This value may be determined using experimental data or computed mathematically using an equation fitted to a data set representative of experimental data.

The value "total percent yield" is the percentage by mass of unaggregated Fc peptide chains and aggregated Fc peptide chains present in a sample produced by a purification step relative to the total amount by mass of unaggregated Fc peptide chains and aggregated Fc peptide chains initially present in the sample subjected to the purification step. This value may be determined using experimental data or computed mathematically using an equation fitted to a data set representative of experimental data.

The value "total percent yield" is different than the value "specific percent yield." The value "specific percent yield" is the percentage by mass of a specific Fc peptide chain present in a sample produced by a purification step relative to the total amount by mass of the specific Fc peptide initially present in the sample subjected to the purification step. For example, if the specific Fc peptide chain is an unaggregated Fc peptide chain then the "specific percent yield" value is the percentage by mass of unaggregated Fc peptide chain present in a sample produced by a purification step relative to the total amount by mass of the specific Fc peptide initially present in the sample subjected to the purification step.

"Total percent yield" values are typically used in the technological field of the invention in conjunction with other parameters, such as a "percent aggregate" value, to describe the results desired or produced by a given purification step or process.

The term "population" means at least two items such as two protein A peptide chains.

The term "protein A" means a peptide chain comprising a sequence with at least 85% identity to SEQ ID NO: 1, SEQ ID NO: 2, SEQ ID NO: 3, SEQ ID NO: 4, or SEQ ID NO: 5 that is capable of binding an Fc peptide chain. SEQ ID NO: 1, SEQ ID NO: 2, SEQ ID NO: 3, SEQ ID NO: 4, or SEQ ID NO: 5 represent respectively the Fc peptide chain binding E, D, A, B, and C domains of *Staphylococcus aureus* protein A. Identity between two peptide chains can be determined by pairwise amino acid sequence alignment using the default settings of the AlignX module of Vector NTI v.9.0.0 (Invitrogen Corp., Carlsbad, Calif.). AlignX uses the CLUSTALW algorithm to perform pair-wise amino acid sequence alignments.

The term "unaggregated" means lacking aggregates as defined supra. For example, an antibody or mimetibody molecule can comprise four individual Fc peptide chains in its unaggregated form (FIG. 1), but will comprise more than four individual Fc peptide chains in its aggregated form.

The present invention provides methods useful for producing a solution of purified Fc peptide chains. The methods employ protein A chromatography to separate high molecular weight, aggregated peptide chains comprising antibody Fc domains from lower molecular weight unaggregated peptide chains that also comprise antibody Fc domains. The solutions of purified Fc peptide chains obtained by the methods of the invention contain less than 5% aggregate at a total percent yield of greater than 70%. These results can be achieved without including detergents or polymers in the aqueous solutions used during the purification.

One aspect of the invention is a method for producing a solution of purified unaggregated Fc peptide chains comprising the steps of providing an aqueous sample comprising unaggregated Fc peptide chains and aggregated Fc peptide chains; contacting the sample with a population of protein A peptide chains bound to an insoluble material and capable of binding greater than 70% of the total mass of unaggregated Fc peptide chains and aggregated Fc peptide chains in the sample; contacting the population of protein A peptide chains with an aqueous solution having a salt concentration of 10 mM to 129 mM and a pH of 3.24 to 3.93; and removing the aqueous solution from contact with the population of protein A peptide chains to produce a solution of purified unaggregated Fc peptide chains comprising less then 5% aggregated Fc peptide chains; wherein the total percent yield of Fc peptide chains is greater than 70%.

Aqueous samples comprising aggregated Fc peptide chains and unaggregated Fc peptide chains may be obtained from a variety of sources. For example, such samples may be cell culture media containing aggregated and unaggregated Fc peptide chains that have been secreted by cells into the media. Alternatively, such samples may be cell culture lysates. Such samples may be obtained from other sources such as lyophilized Fc peptides reconstituted in an aqueous solution. Cells producing aggregated and unaggregated Fc peptide chains may be prokaryotic, eukaryotic, or archeal cells capable of expressing Fc peptide chains.

The method of the invention may be used to purify a genus of Fc peptide chain molecules comprising Fc domains. This genus of Fc peptide chain molecules includes, for example, antibody molecules comprising Fc domains, Fc fusion peptide chains comprising Fc domains, and mimetibody peptide chains comprising Fc domains (FIG. 1). Mimetibody molecules are exemplary representatives of a genus of peptide chains comprising Fc domains.

The unaggregated Fc peptides in the aqueous sample comprise no more than four individual Fc peptide chains. For example, the unaggregated Fc peptide may be an antibody molecule consisting of two antibody heavy chain molecules and two antibody light chain molecules (FIG. 1). Such a molecule contains no more than four Fc peptide chains. One Fc peptide chain is present in the first heavy chain and one is present in the second heavy chain.

The unaggregated Fc peptide may also be a single chain antibody molecule, sometimes referred to as an antibody half-molecule, consisting of one antibody heavy chain molecule and one antibody light chain molecule. Such a molecule contains no more than four Fc peptide chains as it contains only one antibody heavy chain.

The unaggregated Fc peptide may also be a Fc fusion molecule consisting of two identical peptide chains comprising a Fc domain fused to a second peptide chain of interest (FIG. 1). Such a molecule contains no more than four Fc peptide chains. One Fc peptide chain is present in the first heavy chain and one is present in the second heavy chain.

The unaggregated Fc peptide may also be a mimetibody molecule consisting of up to four peptide chains of the generic formula (M-L-V2-H—$C_H2$-$C_H3$). Such a molecule contains no more than four Fc peptide chains.

Unaggregated mimetibody molecules comprise features of both antibody molecules and Fc fusion molecules as shown in FIG. 1 and by the above descriptions. The antibody like features of mimetibody molecules include the antibody derived variable region V2 peptide chain sequences, antibody derived hinge peptide chain sequences, antibody derived heavy chain $C_H2$ constant region peptide chain sequences, and antibody derived $C_H3$ constant region peptide chain sequences. Fc fusion molecule like features of mimetibody molecules include the bioactive M peptide chain, the antibody heavy chain $C_H2$ constant region peptide chain sequences, and antibody $C_H3$ constant region peptide chain sequences. Consequently, mimetibody molecules are representative of both the antibody and Fc fusion classes of molecules (FIG. 1) and of the genus of Fc peptide chains comprising these molecular species (FIG. 1).

In the methods of the invention the aggregated Fc peptides in the aqueous sample comprise more than four individual Fc peptide chains. For example, an aggregated Fc peptide chain may comprise more than two antibody molecules, more than two mimetibody molecules, or more than two Fc fusion molecules that have become associated. Such molecules may become associated through any mechanism such as covalent bonding, hydrophobic interactions or other non-covalent bonding.

Aggregates of three antibody molecules may comprise six antibody heavy chains and six antibody light chains. Such a molecule comprises six Fc peptide chains, one for each antibody heavy chain, and is an aggregated Fc peptide chain because it contains more than four individual Fc peptide chains.

Aggregates of three mimetibody molecules may comprise six antibody derived heavy chain $C_H2$-$C_H3$ peptide chains. Such a molecule comprises six Fc peptide chains, one for each heavy chain $C_H2$-$C_H3$ peptide chain, and is an aggregated Fc peptide chain because it contains more than four individual Fc peptide chains.

Aggregates of Fc fusion molecules may comprise six identical peptide chains that each comprise a Fc domain fused to a second peptide chain of interest. Such a molecule comprises sixFc peptide chains, one for each peptide chain, and is an aggregated Fc peptide chain because it contains more than four individual Fc peptide chains.

Those skilled in the art will recognize other higher order aggregate molecules than those exemplified above (e.g. aggregates of four or more antibody molecules). Additionally, those skilled in the art will recognize that the association of antibody, mimetibody or Fc fusion half-molecules with two whole molecules will produce an aggregated Fc peptide, because such a molecule will comprise five individual Fc peptide chains. Such a molecule is an aggregated Fc peptide chain because it contains more than four individual peptide chains.

A population of protein A peptide chains bound to an insoluble material (protein A conjugate material) suitable for use in the methods of the invention may be provided in many different formats. One such format is, for example, a bead like protein A chromatography resin. Typically, such bead like resins are loaded into a column for chromatography. Mabselect® (GE Healthcare UK Ltd., Little Chalfont Buckinghamshire, UK) protein A chromatography resin is one example of such a format. Mabselect® protein A chromatography resin comprises a population of recombinantly expressed protein A peptide chains that have been conjugated via an epoxy coupling chemistry to an insoluble, highly cross linked agarose material with a diameter of 40 to 130 µM (average diameter is 85 µM). Mabselect® protein A chromatography resin has a dynamic binding capacity of approximately 30 mg human IgG antibody per ml of medium. Dynamic binding capacity is determined at 10% breakthrough by frontal analysis at a mobile phase velocity of 500 cm/h in a column with a bed height of 20 cm. Mabselect SuRe® (GE Healthcare UK Ltd., Little Chalfont Buckinghamshire, UK) is another example of such a format. Mabselect SuRe® protein A chromatography resin is essentially identical to Mabselect® but has been conjugated to protein A peptide chains molecules that tolerate basic pH values. Other formats are plate and capillary formats in which a population of protein A molecules are directly or indirectly bound to an insoluble material which is supplied as a plate or capillary. Those skilled in the art will recognize other formats and insoluble materials such as glass, metal or organic polymers suitable for providing a population of protein A peptide chains bound to an insoluble material.

In the methods of the invention the protein A peptide chains bound to the insoluble material comprise a sequence with at least 85% identity to SEQ ID NO: 1, SEQ ID NO: 2, SEQ ID NO: 3, SEQ ID NO: 4, or SEQ ID NO: 5 that is capable of binding an Fc peptide chain. SEQ ID NO: 1, SEQ ID NO: 2, SEQ ID NO: 3, SEQ ID NO: 4, or SEQ ID NO: 5 represent respectively the amino acid sequences of the Fc peptide chain binding E, D, A, B, and C domains of Staphylococcus aureus protein A. Each of these sequences are, individually, examples of protein A peptide chains. Amino acid residues 1 to 441 of SEQ ID NO: 6 is another example of a protein A peptide chain. The amino acid sequence of SEQ ID NO: 6 corresponds to a portion of the mature form of the Fc peptide chain binding extracellular domain of Staphylococcus aureus protein A spanning the E, D, A, B and C domains. Other examples of such protein A peptide chains include protein A peptide chains produced by isolated Staphylococcus aureus strains or which have been modified to have particular properties such as resistance to basic pH values. Those skilled in the art will recognize additional examples of such protein A peptide chains.

Typically in the methods of the invention, insoluble protein A conjugated materials are equilibrated with an appropriate buffer solution prior to contact with an aqueous sample comprising aggregated and unaggregated Fc peptides. A solution containing 50 mM $NaH_2PO_4$ and 150 mM NaCl at pH 7.4 is an example of one such equilibration buffer. A solution containing 50 mM $NaH_2PO_4$, 150 mM NaCl, and 0.1% polysorbate-80 at pH 7.4 is another example of one such equilibration buffer. A solution containing 0.05 M boric acid, 4.0 M NaCl, at a pH of 9.0 is another example of such an equilibration buffer. Protein A conjugated materials can be equilibrated with a particular buffer solution by contacting the material with the solution for a time sufficient for equilibration to occur. After equilibration protein A conjugated materials may be washed with equilibration buffer or equivalent solutions to remove residual impurities such as particulates or contaminating molecules. Additional equilibration buffer compositions and techniques suitable for preparing protein A conjugate materials for use in the methods of the invention are well know to those of ordinary skill in the art.

Aggregated and unaggregated Fc peptides in an aqueous sample will bind to protein A conjugate material under a range of conditions. Aggregated and unaggregated Fc peptides in an aqueous sample contacted with protein A conjugate materials typically will bind to such materials when the pH value of the sample is about 6.0 to 8.0. The time of contact necessary for optimal binding is readily determined empirically, and is typically on the order of minutes.

Aggregated and unaggregated Fc peptides in aqueous samples comprising standard buffered eukaryotic cell culture media compositions will bind to protein A conjugate materials. Serum free AIM-V® cell culture media (Invitrogen Inc., Carlsbad, Calif.) and Roswell Park Memorial Institute 1640 (RPMI-1640) cell culture media with pH values of about 5.6 to 7.4 are two examples of such standard buffered eukaryotic cell culture media compositions. Aggregated and unaggregated Fc peptide present in other aqueous compositions such as phosphate buffer saline (PBS) at a pH value of 7.4 of will also bind to protein A conjugate materials.

In some instances salts, detergents, or other molecules may need to be added to an aqueous sample or solution to facilitate binding of Fc peptides in to protein A conjugate materials. Those skilled in the art will recognize additional aqueous samples and solution compositions suitable for contacting with protein A conjugate materials and ensuring binding of Fc peptide chains present in the sample.

In the methods of the invention, a population of protein A peptide chains bound to an insoluble material must be able to bind greater than 70% of the total mass of unaggregated Fc peptide chains and aggregated Fc peptide chains present in a sample. One can determine the binding capacity of such a protein A conjugate material using standard methods. For example, standard size exclusion HPLC (SE-HPLC) and standard protein assay methods can be used to determine the unaggregated Fc peptide content of an aqueous sample prior to contact with a protein A conjugate material. A volume of the aqueous sample can then be contacted with the protein A conjugate material for a time sufficient for binding to occur. The aqueous sample is then removed from contact with the protein A conjugate material and the unaggregated Fc peptide chain and aggregated Fc peptide chain content of the resulting aqueous sample is determined. The protein A conjugate material is able to bind greater than 70% of the total mass of unaggregated Fc peptide chains and aggregated Fc peptide chains present in a sample when these resulting sample contains less than 30% of the total mass of unaggregated Fc peptide chains and unaggregated Fc peptide chains originally present in the aqueous sample. Those skilled in the art will recognize other techniques, such as dynamic binding capacity measurement techniques, for determining the binding capacity of protein A conjugate material. Additionally, those skilled in the art will recognize that the time of contact with the protein A conjugate and other parameters such as the salt concentration or pH of the aqueous sample comprising the Fc peptide chains can be adjusted to optimize the binding capacity of a given protein A conjugate material and the suitability of the material for use in the methods of the invention.

In the methods of the invention the population a protein A peptide chains bound to an insoluble material are contacted with an aqueous solution having a salt concentration of 10 mM to 129 mM and a pH of 3.24 to 3.93. This results in binding of both aggregated and unaggregated Fc peptide chains to the protein A conjugate material. It is believed that contact with the aqueous solution having a salt concentration of 10 mM to 129 mM and a pH of 3.24 to 3.93 causes unaggregated Fc peptide chains bound to the protein A peptide chains to enter the aqueous solution at a faster rate than bound Fc peptide chain aggregates. The result is that a solution of purified Fc peptide chains comprising less than 5% aggregated Fc peptide chain is obtained at a total percent yield of Fc peptide chains greater than 70%.

In the methods of the invention the aqueous solution having a salt concentration of 10 mM to 129 mM and a pH of 3.24 to 3.93 can be contacted with the protein A conjugate material by the use of a step gradient, a non-stepped gradient, or a hybrid gradient. In a step gradient each "step" involves contacting the population of protein A molecules with an aqueous solution of a specific composition for a specific period of time. Step gradients may comprise single or multiple steps that result in the aqueous solution having a salt concentration of 10 mM to 129 mM and a pH of 3.24 to 3.93 being contacted with the protein A conjugate material. In a non-stepped gradient the gradient may be linear or non-linear (e.g. exponential) and the composition of the aqueous solution contacted with the protein A conjugate material is varied continuously in a linear or non-linear fashion over a period of time. Non-stepped gradients result an aqueous solution having a salt concentration of 10 mM to 129 mM and a pH of 3.24 to 3.93 being contacted with the protein A conjugate material at a specific point in time during application of the non-stepped gradient. Step gradients and non-stepped gradients may also be combined to generate hybrid gradients. Those skilled in the art will recognize other methods for contacting a population of protein A peptide chains with an aqueous solution having a salt concentration of 10 mM to 129 mM and a pH of 3.24 to 3.93.

In the methods of the invention an aqueous solution which has a salt concentration of 10 mM to 129 mM and a pH of 3.24 to 3.93 is removed from contact with the protein A conjugate material that has bound the aggregated and unaggregated Fc peptide chains. This produces a solution of purified Fc peptide chains that comprise less than 5% aggregated Fc peptide chains at a total percent yield value of Fc peptide chains greater than 70%. These total percent yield and percent aggregate values are achieved, in part, by collecting the entire volume of the aqueous solution having a salt concentration of 10 mM to 129 mM and a pH of 3.24 to 3.93 that had been contacted with the protein A conjugate material. This can be accomplished on a protein A chromatography column by contacting the aqueous solution having a salt concentration of 10 mM to 129 mM and a pH of 3.24 to 3.93 with protein A conjugated resin materials packed in the column and collecting the entire volume of aqueous solution subsequently eluted from the column. In this way, the entire population of unaggregated Fc peptide chains eluted from the column is collected which ensures a total percent yield of Fc peptide chains greater than 70%. Importantly, the bulk of aggregated Fc peptide chains to remain bound to the protein A conjugate material on the column such that the entire volume of eluted aqueous solution contains less than 5% aggregate. Alternatively, those skilled in the art will recognize that other parameters such as the protein concentration, conductivity, pH, and unaggregated Fc peptide chain content of the aqueous solution contacted with the population of protein A peptide chains may be monitored to ensure that the total percent yield of Fc peptide chain in the resulting solution of purified Fc peptide chains is greater than 70%.

In the methods of the invention aggregated Fc peptide chain and unaggregated Fc peptide chain content in an aqueous sample or purified solution can be measured using standard size exclusion HPLC (SE-HPLC) and protein assay methods. The measured values can then be used to determine the aggregated Fc peptide content of a solution of purified Fc peptide chains obtained by the methods of the invention. Those skilled in the art will recognize other techniques for detecting aggregated and unaggregated Fc peptide chains (e.g. non-denaturing gel electrophoresis) and protein content that can be used to ascertain the percentage of aggregated Fc peptide chains in a solution of purified Fc peptide chains.

In the methods of the invention unaggregated Fc peptide chain content in an aqueous sample or purified Fc peptide chain solution can be measured using standard size exclusion HPLC (SE-HPLC) and protein assay methods as described above. The measured values can then be used to determine the unaggregated Fc peptide chain content of a solution of purified Fc peptide chains obtained by the methods of the invention and the unaggregated Fc peptide chain content of the aqueous sample subjected to the methods of the invention. These values can then be used to ascertain the total percent yield of Fc peptide chains in the solution of purified Fc peptide chains produced by the methods of the invention. These values can also be used to ascertain the specific percent yield of the unaggregated Fc peptide chains in the solution of purified Fc peptide chains produced by the methods of the invention.

In one embodiment of the method of the invention the population of protein A peptide chains bound to an insoluble material has a height equivalent to a theoretical plate value of 0.005 cm to 0.05 cm. Height equivalent to a theoretical plate (HETP) values are a measure of the separation efficiency of chromatographic materials such as protein A conjugate materials. Methods for determining the HETP value for chromatographic materials such as a protein A conjugate materials are well known in the art. Such methods are also described in Martin and Synge, 35 *Biochem. J.* 1358 (1941).

In another embodiment of the method of the invention the salt is tris(hydroxymethyl)aminomethane acetate.

In another embodiment of the method of the invention the unaggregated Fc peptide chain is a mimetibody. One example of a mimetibody which may be purified using this embodiment of the invention is the mimetibody with the amino acid sequence described by SEQ ID NO: 7. Those skilled in the art will recognize other mimetibody molecules.

Another aspect of the invention is a method for producing a solution of purified unaggregated Fc peptide chains comprising the steps of providing an aqueous sample comprising unaggregated Fc peptide chains and aggregated Fc peptide chains; contacting the sample with a population of protein A peptide chains bound to an insoluble material and capable of binding greater than 70% of the total mass of unaggregated Fc peptide chains and aggregated Fc peptide chains in the sample; contacting the population of protein A peptide chains with an aqueous solution having a salt concentration of 41 mM to 97 mM and a pH of 3.42 to 3.74; and removing the aqueous solution from contact with the population of protein A peptide chains to produce a solution of purified unaggregated Fc peptide chains comprising less then 5% aggregated Fc peptide chains; wherein the total percent yield of Fc peptide chains is greater than 70%.

In one embodiment of the method of the invention the population of protein A peptide chains bound to an insoluble material has a height equivalent to a theoretical plate value of 0.005 cm to 0.05 cm.

In another embodiment of the method of the invention the salt is tris(hydroxymethyl)aminomethane acetate.

In another embodiment of the method of the invention the unaggregated Fc peptide chain is a mimetibody.

Another aspect of the invention is a method for producing a solution of purified unaggregated Fc peptide chains comprising the steps of providing an aqueous sample comprising unaggregated Fc peptide chains and aggregated Fc peptide chains; contacting the sample with a population of protein A peptide chains bound to an insoluble material and capable of binding greater than 70% of the total mass of unaggregated Fc peptide chains and aggregated Fc peptide chains in the sample; contacting the population of protein A peptide chains with an aqueous solution having a salt concentration of 55 mM to 85 mM and a pH of 3.50 to 3.66; and removing the aqueous solution from contact with the population of protein A peptide chains to produce a solution of purified unaggregated Fc peptide chains comprising less then 5% aggregated Fc peptide chains; wherein the total percent yield of Fc peptide chains is greater than 70%.

In one embodiment of the method of the invention the population of protein A peptide chains bound to an insoluble material has a height equivalent to a theoretical plate value of 0.005 cm to 0.05 cm.

In another embodiment of the method of the invention the salt is tris(hydroxymethyl)aminomethane acetate.

In another embodiment of the method of the invention the unaggregated Fc peptide chain is a mimetibody.

Another aspect of the invention is a method for producing a solution of purified unaggregated mimetibody Fc peptide chains comprising the steps of providing an aqueous sample comprising unaggregated mimetibody Fc peptide chains and aggregated mimetibody Fc peptide chains; contacting the sample with a population of protein A peptide chains bound to an insoluble material and capable of binding greater than 70% of the total mass of unaggregated mimetibody Fc peptide chains and aggregated mimetibody Fc peptide chains in the sample; contacting the population of protein A peptide chains with an aqueous solution having a tris(hydroxymethyl)aminomethane acetate salt concentration of 55 mM to 85 mM and a pH of 3.50 to 3.66; and removing the aqueous solution from contact with the population of protein A peptide chains to produce a solution of purified unaggregated mimetibody Fc peptide chains comprising less then 5% aggregated mimetibody Fc peptide chains; wherein the total percent yield of mimetibody Fc peptide chains is greater than 70%.

In one embodiment of the method of the invention the population of protein A peptide chains bound to an insoluble material has a height equivalent to a theoretical plate value of 0.005 cm to 0.05 cm.

The present invention will now be described with reference to the following specific, non-limiting examples.

EXAMPLE 1

Protein A Chromatography Separation of Aggregated and Unaggregated Antibody Fc Domains Protein A chromatography can be used to separate aggregated and unaggregated peptide chains comprising antibody Fc domains (Fc peptide chains) when specific elution conditions are used (Table 1).

TABLE 1

Results of Protein A Chromatography Experiment

| Sample | Chromatographic Step pH | Protein Concentration (mg/mL) | Sample Volume (mL) | Total Protein (mg) | Percent Aggregate (%) |
|---|---|---|---|---|---|
| C1374C Cell Culture Supernatant | — | 1.8 | 112.8 | 203.0 | 10.1 |
| Second Wash | 5.0 | 0.004 | 56.6 | 0.24 | — |
| Elution | 3.6 | 5.4 | 29.1 | 156.2 | 1.32 |
| Strip | 3.0 | 1.2 | 33.9 | 41.58 | 41.9 |

90% of aggregated Fc peptide chains loaded onto a protein A chromatography column were separated from unaggregated Fc peptide chains when the column elution buffer comprised 50 mM sodium acetate at a pH of 3.6 (Table 1).

Protein A specifically binds antibody Fc domains when such domains are present and accessible in a peptide chain. Protein A chromatography under standard conditions yields a purified mixture of both aggregated Fc peptide chains and unaggregated Fc peptide chains since both classes of molecules comprise Fc domains. Consequently, in the present invention, the selection of protein A chromatography column elution conditions that could separate unaggregated Fc peptide chains from aggregated Fc peptide chains (Table 1) when both classes of peptide chains are present in a mixture loaded on a Protein A chromatography column was not taught or suggested in the art.

Cell culture supernatant samples containing both unaggregated and aggregated Fc peptide chains as well as other non-Fc peptide chains were produced by culturing eukaryotic C1374C cells. C1374C cells secrete recombinant mimetibody peptide chains and other peptide chains into the cell culture media surrounding these cells. Unaggregated mimetibody peptide chains expressed by C1374C cells have the generic formula (I):

$$(M\text{-}L\text{-}V2\text{-}H\text{—}C_H2C_H3)_{(t)} \qquad (I)$$

where M is an erythropoietin receptor binding molecule, t is an integer less than, or equal to, 4 and the other constituents are as defined supra. The $C_H2\text{-}C_H3$ portion of the mimetibody expressed by C1374C cells comprises a portion of an antibody Fc domain and can be bound by protein A. Standard size exclusion high performance liquid chromatography (SE-HPLC) analyses indicate that C1374C cell culture supernatant contains both high molecular weight Fc domain comprising mimetibody aggregates (e.g. mimetibody molecules with t>4) and unaggregated Fc domain comprising mimetibody molecules with t≤4 (Table 1) in additional to other peptide chains lacking Fc domains. The desired unaggregated mimetibody product molecule consisted of four peptide chains of the generic formula (M-L-V2-H—$C_H2$-$C_H3$).

C1374 C cells were cultured at 37° C. in serum free, chemically defined media under standard cell culture conditions. C1374C cell culture supernatants containing between 1 mg/ml and 2 mg/ml of total protein were then collected for subsequent chromatography analyses.

Protein A chromatography to separate aggregated and unaggregated Fc peptide chains was performed as follows. Chromatography was performed at a temperature between 19° C. and 25° C. First, the resin in a Mabselect® (GE Healthcare UK Ltd., Little Chalfont Buckinghamshire, UK) protein A chromatography column was equilibrated in a solution containing 50 mM $NaH_2PO_4$ and 150 mM NaCl at pH 7.4 and the baseline $A_{280\ nm}$ value was measured. The $A_{280\ nm}$ value is a measure of the peptide chain concentration in a solution such as column effluent. Second, 112.8 ml of C1374C cell culture supernatant containing 1.8 mg total protein per ml of supernatant was loaded onto the protein A chromatography column. SE-HPLC demonstrated the supernatant sample loaded contained 20.50 mg of aggregated Fc peptide chains. Third, resin in the column was washed a first time with a solution containing 50 mM $NaH_2PO_4$ and 150 mM NaCl at pH 7.4 until the measured $A_{280\ nm}$ value returned to the baseline value. Fourth, the column was washed a second time with a solution of 100 mM $NaCH_3COO$ at pH 5.0 and column effluent samples were collected. Fifth, peptide chains bound to the protein A chromatography column resin were eluted with a solution of 50 mM $NaCH_3COO$ at pH 3.6 and column effluent samples were collected. Last, peptide chains remaining bound to the protein A chromatography column were stripped off the column resin with a solution of 100 mM $NaCH_3COO$ at pH 3.0 and column effluent samples were collected. Protein concentration in both supernatant and column effluent samples was then determined using standard methods. Aggregated Fc peptide chain content in these samples was also determined using standard SE-HPLC methods.

Using a solution of 50 mM $NaCH_3COO$ at pH 3.6 to elute Fc peptide chains from a protein A resin chromatography column separated 90% of the aggregated Fc peptide chains initially present in C1374C cell culture supernatant from unaggregated Fc peptide chains (Table 1). Specifically, 20.50 mg of Fc peptide chain aggregate was present in the C1374C cell culture supernatant sample loaded onto the protein A chromatography column, but only 2.06 mg of Fc peptide chain aggregate was eluted from the resin with a solution of 50 mM $NaCH_3COO$ at pH 3.6. This 2.06 mg mass of Fc peptide chain aggregate comprised only 1.32% of the total peptide chain mass present in the sample collected after elution. The remaining peptide chain mass in the sample collected after elution comprised unaggregated mimetibody Fc peptide chains. This remaining peptide chain mass represented a total percent yield of 76.9% by mass of the unaggregated and aggregated mimetibody Fc peptide chains originally loaded onto the protein A chromatography column. Stripping the protein A chromatography column resin with a solution of 100 mM $NaCH_3COO$ at pH 3.0 resulted in the recovery of 17.42 mg of Fc peptide chain aggregate. This 17.42 mg mass represented a specific percent yield value of 85.0% of the Fc aggregate mass loaded onto the column. Together this data indicates that protein A column chromatography can be used to separate aggregated and unaggregated Fc peptide chains when specific salt concentration values and pH values are used in the elution step.

EXAMPLE 2

Figure 2:
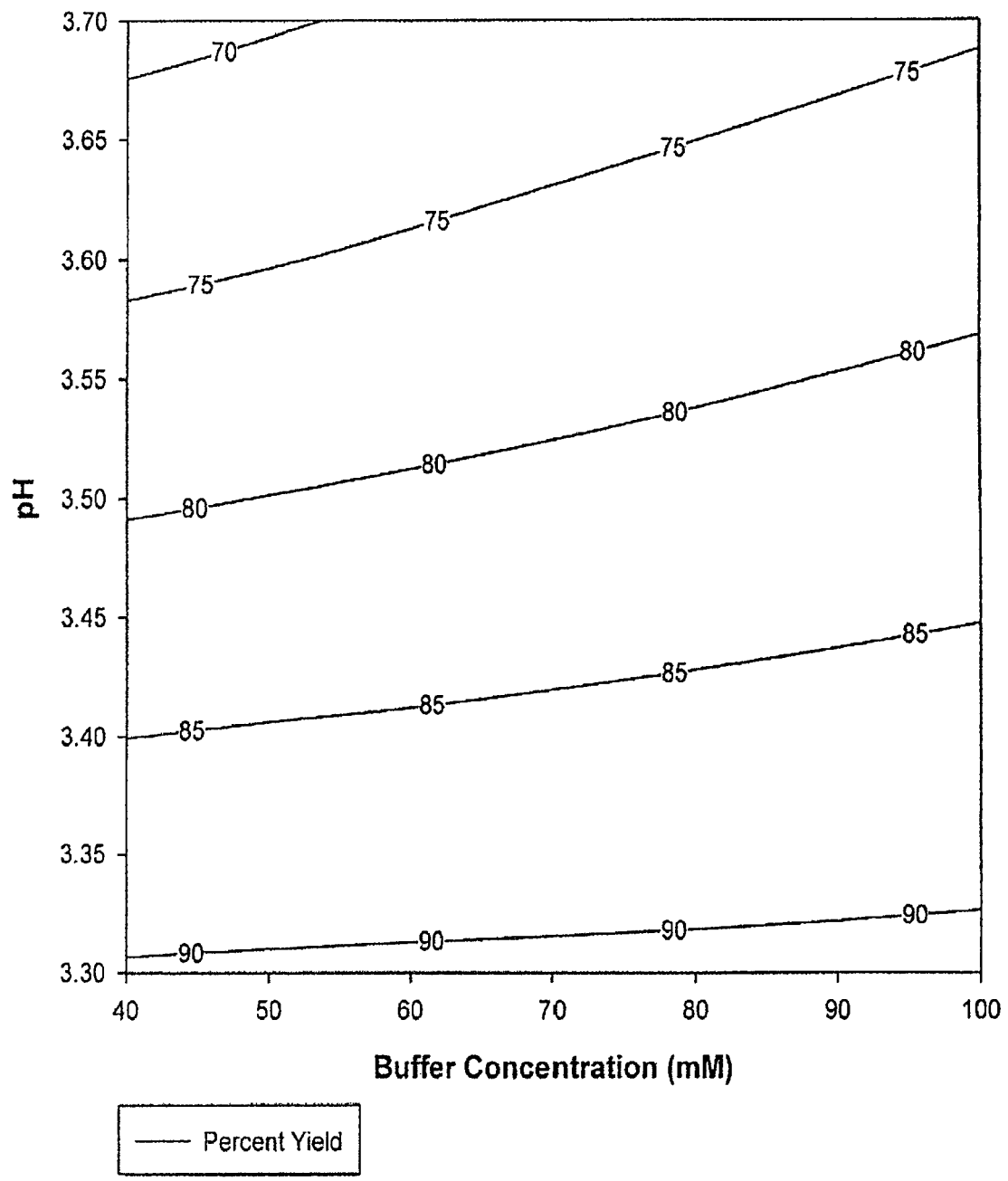
FIG. 2 Plot of the fitted TotalPercentYield(x,y) equation. Total percent yield values are shown as a function of buffer tris(hydroxymethyl)aminomethane acetate salt concentration in mM and pH.

Total Percent Yield of Fc Peptide Chains after Protein a Chromatography is a Function of Elution Buffer Salt Concentration and pH The total percent yield by mass of Fc peptide chains recovered after elution from the protein A chromatography column is a function of elution buffer tris(hydroxymethyl)aminomethane acetate salt concentration and pH (Table 2 and FIG. 2).

TABLE 2

Results of Protein A Chromatography Experiments

| Elution Buffer pH | Elution Buffer Concentration (mM) | Elution Protein Concentration (mg/mL) | Percent Aggregate in Elution (%) | Total Percent Yield (%) | Objective Function |
|---|---|---|---|---|---|
| 3.7 | 40 | 5.14 | 1.2 | 68.42 | 0.000 |
| 3.7 | 100 | 5.95 | 1.86 | 74.5 | 0.307 |
| 3.3 | 100 | 18.00 | 9.16 | 91.11 | 0.000 |
| 3.3 | 40 | 14.13 | 6.65 | 90.34 | 0.000 |
| 3.5 | 70 | 10.50 | 2.98 | 81.15 | 0.387 |
| 3.4 | 80 | 14.39 | 5.29 | 89.49 | 0.000 |
| 3.5 | 60 | 9.76 | 2.04 | 78.01 | 0.396 |
| 3.5 | 60 | 10.09 | 2.09 | 80.61 | 0.457 |
| 3.4 | 60 | 11.57 | 3.67 | 83.22 | 0.342 |
| 3.6 | 60 | 6.56 | 1.83 | 75.16 | 0.330 |

Total percent yield values from the experimental data represents the percentage by mass of unaggregated Fc peptide chains and aggregated Fc peptide chains present in the purified sample recovered after elution relative to the total amount by mass of unaggregated Fc peptide chain and aggregated Fc peptide present in the supernatant sample originally loaded onto the protein A chromatography column. The total percent yield value is a measure of the efficient recovery of both unaggregated Fc peptide and aggregated Fc peptide chain molecules after elution from a protein A chromatography column. For these experiments C1374C cell culture, supernatant collection, protein A chromatography column preparation, column equilibration, and supernatant loading were performed as described in Example 1 above. Chromatography was performed at a temperature between 19° C. and 25° C. Resin in the column was first washed with a solution containing 50 mM $NaH_2PO_4$ and 150 mM NaCl at pH 7.4 until the measured $A_{280\ nm}$ value returned to the baseline value. The column was then washed a second time with a solution of 100 mM tris(hydroxymethyl)aminomethane acetate salt ($NH_2C(CH_2OH)_3$.$CH_3COOH$; (JT Baker, Phillipsburg, N.J.) at pH 5.0. Peptide chains bound to the protein A chromatography column resin were eluted in each individual protein A chromatography experiment with a solution of tris(hydroxymethyl)aminomethane acetate salt ($NH_2C(CH_2OH)_3$.$CH_3COOH$; (JT Baker, Phillipsburg, N.J.) at the concentrations and pH values indicated in Table 2. The elution buffer salt concentration and pH value were both varied in each individual experiment. Protein concentrations and aggregated Fc peptide chain content in samples was determined using standard SE-HPLC methods as described in Example 1 above.

The total percent yield values (z axis values) obtained from these experiments were then plotted (data not shown) as a function of elution buffer tris(hydroxymethyl)aminomethane acetate salt concentration (x axis value) and pH value (y axis value). Standard polynomial curve fitting was then performed using the least squares method to obtain an optimized polynomial equation fitted to the plotted experimental data.

The polynomial equation obtained was designated the "TotalPercentYield" equation. The TotalPercentYield equation reveals that the total percent yield value (z axis) obtained by protein A chromatography can be described mathematically as a function of both elution buffer tris(hydroxymethyl)aminomethane acetate salt concentration (x axis value) and pH (y axis value). The TotalPercentYield function is:

$$\text{TotalPercentYield}(x,y) = -0.676x + 0.209xy - 62.4y + 295.747$$

where
x=tris(hydroxymethyl)aminomethane acetate salt concentration; mM
and
y=pH

A graphical plot of the TotalPercentYield function is shown in FIG. 2. These analyses reveal that the total percent yield by mass of Fc peptide chains after elution from the protein A chromatography column is a function of elution buffer tris(hydroxymethyl)aminomethane acetate salt concentration and pH (Table 2 and FIG. 2).

In order to optimally use protein A column chromatography for the preparation of biopharmaceuticals the TotalPercentYield value must be greater than 70%. The functional relationships described by the TotalPercentYield function can be used to identify protein A chromatography conditions that produce such optimal TotalPercentYield values (e.g. >70%).

EXAMPLE 3

Figure 3:
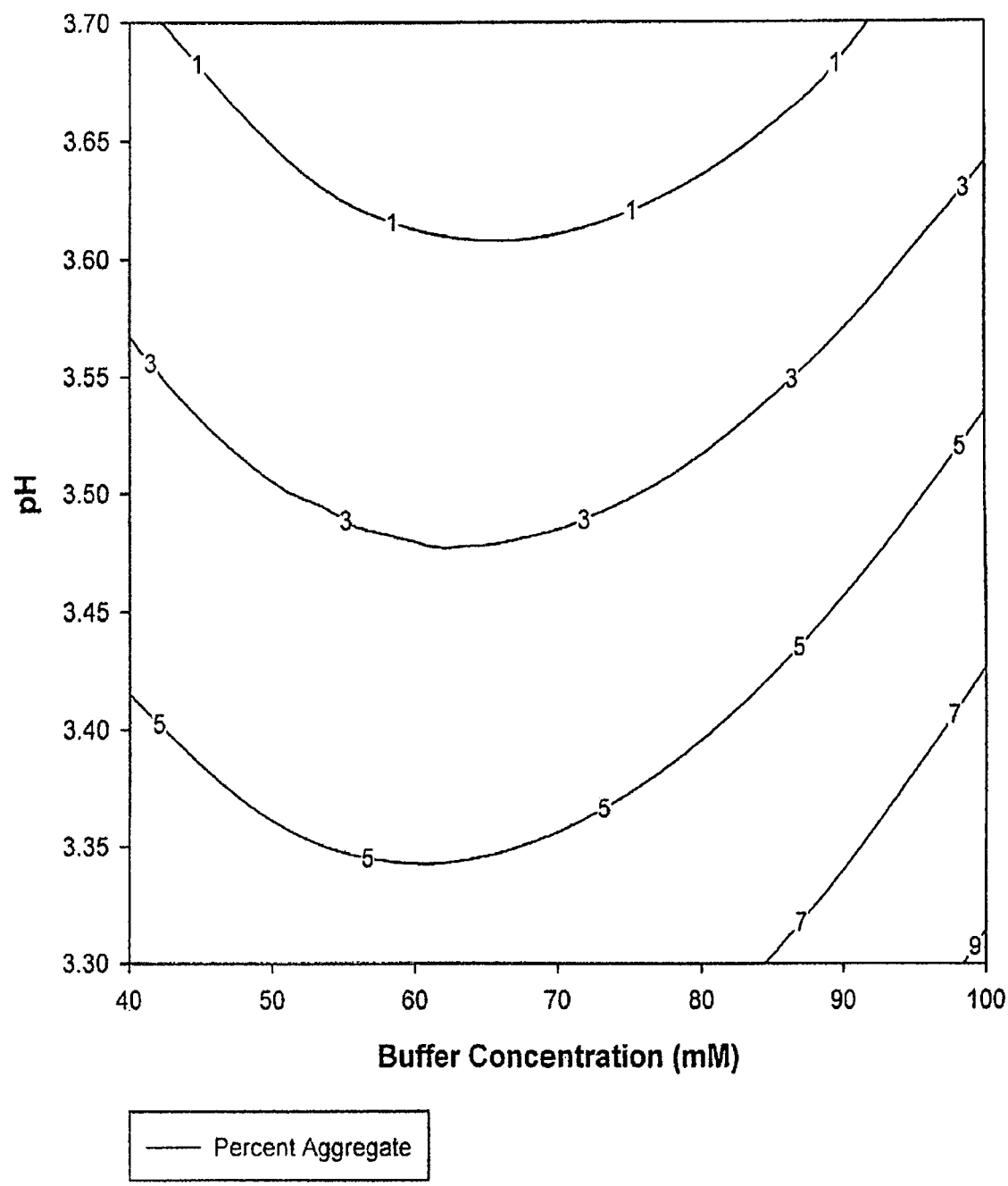
FIG. 3 Plot of the fitted PercentAggregate(x,y) equation. Percent aggregate values are shown as a function of buffer tris(hydroxymethyl)aminomethane acetate salt concentration in mM and pH.

Percent Aggregated Fc Peptide Chains in Protein a Chromatography Eluantes is a Function of Elution Buffer Salt Concentration and pH The percentage of aggregated Fc peptide chains by mass in eluted samples recovered after protein A chromatography column purification is a function of elution buffer tris(hydroxymethyl)aminomethane acetate salt concentration and pH (Table 2 and FIG. 3). Percent aggregate values from the experimental data represent the percentage by mass of aggregated Fc peptide chain present in the purified sample recovered after elution relative to the total amount by mass of all Fc peptide chains, both aggregated and unaggregated, present in this sample. The percent aggregate value is a measure of the aggregated Fc peptide chain contamination level in the eluted sample recovered after protein A chromatography. Stated differently, percent aggregate is a measure of the purity of the eluted sample recovered.

Eluted samples were those produced by the protein A chromatography experiments described in Example 2 above. Elution buffer tris(hydroxymethyl)aminomethane acetate salt concentration and pH value were both varied in each individual experiment (Table 2). Protein concentrations and aggregated Fc peptide chain content in these samples was determined using standard SE-HPLC methods as described in Example 1 above.

The percent aggregate values (z axis values) obtained from these experiments were then plotted (data not shown) as a function of elution buffer tris(hydroxymethyl)aminomethane acetate salt concentration (x axis value) and pH value (y axis value). Standard polynomial curve fitting was then performed using the least squares method to obtain an optimized polynomial equation fitted to the plotted experimental data.

The polynomial equation obtained was designated the "PercentAggregate" equation. The PercentAggregate equation reveals that the percent aggregate value (z axis) obtained by protein A chromatography can be described mathematically as a function of both elution buffer tris(hydroxymethyl)aminomethane acetate salt concentration (x axis value) and pH (y axis value). The PercentAggregate function is:

$$\text{PercentAggregate}(x,y) = 0.00242x^2 - 0.0213x - 0.0819xy - 1.576y^2 + 0.551y + 29.680$$

where
x=tris(hydroxymethyl)aminomethane acetate salt concentration; mM
and
y=pH

A graphical plot of the PercentAggregate function is shown in FIG. 3. These analyses reveal that percent aggregate by mass in eluted samples recovered after protein A chromatography column purification is a function of elution buffer tris(hydroxymethyl)aminomethane acetate salt concentration and pH (Table 2 and FIG. 3).

In order to optimally use protein A column chromatography for the preparation of biopharmaceuticals the PercentAggregate value must be less than 5%. The functional relationships described by the PercentAggregate function can be used to identify protein A chromatography conditions that produce such optimal PercentAggregate values (e.g. <5%).

EXAMPLE 4

Selection of Protein a Chromatography Elution Buffer Salt and pH Values for Optimal Total Percent Yield and Percent Aggregate Values Protein A chromatography elution buffer salt and pH values for obtaining eluate samples with optimal Fc peptide chain total percent yield and percent aggregate values were identified using mathematical optimization problem solving techniques.

First, optimal TotalPercentYield values for the preparation of biopharmaceuticals comprising Fc peptide chains were selected. The optimal TotalPercentYield values selected must be greater than 70% (see Example 2 above). This optimal set of TotalPercentYield values can be expressed mathematically using the following fuzzy set:

$$m(TotalPercentYield) = \begin{cases} 0, & \text{if } TotalPercentYield \leq 70 \\ \frac{(TotalPercentYield - 70)}{(100 - 70)}, & \text{if } 70 < TotalPercentYield < 100 \\ 1, & \text{if } TotalPercentYield \geq 100 \end{cases}$$

As shown in Example 3 above, the TotalPercentYield value is a function of the tris(hydroxymethyl)aminomethane acetate salt concentration and the pH of the protein A chromatography elution buffer.

The value of the fuzzy set m(TotalPercentYield) can be calculated using either of two methods. In the first method, the m(TotalPercentYield) value at a given protein A chromatography elution buffer salt concentration and pH value is calculated using the experimentally determined total percent yield value (Table 2) from an individual chromatography experiment. In the second method, the m(TotalPercentYield) value at a given protein A chromatography elution buffer salt concentration and pH value can be calculated using the polynomial TotalPercentYield function fitted by the least squares method to the experimentally determined total percent yield value data set (Table 2).

The value of the fuzzy set m(TotalPercentYield) will be 0 if the total percent yield is less than 70% at a given salt concentration and pH value. The value of the fuzzy set m(TotalPercentYield) is equal to (TotalPercentYield-70)/(100-70) when the total percent yield is greater than 70% and less than 100%. For example, If the total percent yield is 80% then m(TotalPercentYield) equals (80-70)/(100-70) or 0.3. Alternatively, the value of the fuzzy set m(TotalPercentYield) will be 1 if the total percent yield is greater than or equal to 100% at a given salt concentration and pH value.

Second, optimal PercentAggregate values for the preparation of biopharmaceuticals comprising Fc peptide chains were then selected. The optimal PercentAggregate values selected must be less than 5% (see Example 2 above). This can be expressed mathematically using the following fuzzy set:

$$m(PercentAggregate) = \begin{cases} 1, & \text{if } PercentAggregate \leq 0 \\ \frac{(5 - PercentAggregate)}{(5 - 0)}, & \text{if } 5 > PercentAggregate > 0 \\ 0, & \text{if } PercentAggregate \geq 5 \end{cases}$$

As shown in Example 3 above, the PercentAggregate value is a function of the tris(hydroxymethyl)aminomethane acetate salt concentration and the pH of the protein A chromatography elution buffer.

The value of the fuzzy set m(PercentAggregate) can be calculated using either of two methods. In the first method, the m(PercentAggregate) value at a given protein A chromatography elution buffer salt concentration and pH value is calculated using the experimentally determined percent aggregate value (Table 2) from an individual chromatography experiment. In the second method, the m(PercentAggregate) value at a given protein A chromatography elution buffer salt concentration and pH value can be calculated using the polynomial PercentAggregate function fitted by the least squares method to the experimentally determined percent aggregate value data set (Table 2).

The value of the fuzzy set m(PercentAggregate) will be 1 if the percent aggregate is less than or equal to 0% at a given salt concentration and pH value. The value of the fuzzy set m(PercentAggregate) is equal to (5-PercentAggregate)/(5-0) when the percent aggregate is greater than 0% and less than 5%. For example, If the percent aggregate is 2% then m(PercentAggregate) equals (5-2)/(5-0) or 0.6. Alternatively, the value of the fuzzy set m(PercentAggregate) will be 0 if the percent aggregate is greater than or equal to 5% at a given salt concentration and pH value.

Third, the m(TotalPercentYield) and m(PercentAggregate) fuzzy set values generated for a given elution buffer salt concentration and pH were used to calculate objective function values using the following "ObjectiveFunction1" equation:

ObjectiveFunction1 = $[m(TotalPercentYield) * m(PercentAggregate)]^{1/2}$

The calculated objective function values (z axis) were then plotted as a function of protein A chromatography elution buffer tris(hydroxymethyl)aminomethane acetate salt concentration (x axis and pH (y axis) (data not shown). Standard polynomial curve fitting was then performed using the least squares method to obtain an optimized polynomial equation fitted to the plotted data. The polynomial equation obtained was designated the "ObjectiveFunction2" equation.

The m(TotalPercentYield) and m(PercentAggregate) fuzzy set values used to calculate the ObjectiveFunction1 values plotted and used to generate the fitted ObjectiveFunction2 equation were calculated using data from either of two sources. For example, some of the ObjectiveFunction1 values plotted were calculated using experimentally determined total percent yield and percent aggregate values (Table 2). Other ObjectiveFunction1 values plotted (Table 3) were

TABLE 3

ObjectiveFunction1 values calculated using the fitted TotalPercentYield and PercentAggregate polynomial equations.

| Buffer Concentration (mM) | pH | Total Percent Yield (%) | Percent Aggregate (%) | Objective Function 1 |
|---|---|---|---|---|
| 40 | 3.35 | 87.64 | 5.84 | 0.000 |
| 40 | 3.45 | 82.23 | 4.55 | 0.193 |
| 40 | 3.55 | 76.83 | 3.23 | 0.284 |
| 40 | 3.45 | 82.23 | 4.55 | 0.193 |
| 41 | 3.52 | 78.51 | 3.52 | 0.290 |
| 42 | 3.53 | 78.03 | 3.29 | 0.303 |
| 43 | 3.54 | 77.56 | 3.06 | 0.313 |
| 44 | 3.55 | 77.09 | 2.83 | 0.320 |
| 45 | 3.54 | 77.68 | 2.88 | 0.330 |
| 46 | 3.53 | 78.27 | 2.93 | 0.338 |
| 47 | 3.52 | 78.86 | 2.99 | 0.344 |
| 48 | 3.58 | 75.78 | 2.08 | 0.335 |
| 49 | 3.59 | 75.33 | 1.86 | 0.334 |
| 50 | 3.35 | 87.87 | 5.14 | 0.000 |
| 50 | 3.45 | 82.67 | 3.77 | 0.323 |
| 50 | 3.55 | 77.48 | 2.36 | 0.363 |
| 50 | 3.51 | 79.56 | 2.93 | 0.363 |
| 51 | 3.52 | 79.10 | 2.73 | 0.371 |
| 52 | 3.53 | 78.64 | 2.53 | 0.377 |
| 53 | 3.54 | 78.19 | 2.34 | 0.381 |
| 54 | 3.55 | 77.74 | 2.14 | 0.384 |
| 55 | 3.35 | 87.99 | 4.97 | 0.000 |
| 55 | 3.45 | 82.90 | 3.55 | 0.354 |
| 55 | 3.50 | 80.35 | 2.83 | 0.387 |
| 55 | 3.60 | 75.26 | 1.36 | 0.357 |
| 55 | 3.56 | 77.29 | 1.95 | 0.385 |
| 55 | 3.35 | 87.99 | 4.97 | 0.000 |
| 56 | 3.57 | 76.85 | 1.76 | 0.385 |
| 56 | 3.36 | 87.50 | 4.80 | 0.152 |
| 57 | 3.58 | 76.42 | 1.58 | 0.383 |
| 57 | 3.37 | 87.02 | 4.64 | 0.202 |
| 58 | 3.59 | 75.99 | 1.40 | 0.379 |
| 58 | 3.38 | 86.55 | 4.48 | 0.240 |
| 59 | 3.60 | 75.56 | 1.22 | 0.374 |
| 59 | 3.39 | 86.08 | 4.32 | 0.269 |
| 60 | 3.35 | 88.10 | 4.90 | 0.112 |
| 60 | 3.45 | 83.12 | 3.43 | 0.370 |
| 60 | 3.55 | 78.13 | 1.94 | 0.407 |
| 60 | 3.50 | 80.62 | 2.69 | 0.404 |
| 60 | 3.65 | 73.14 | 0.43 | 0.309 |
| 60 | 3.42 | 84.61 | 3.88 | 0.331 |
| 60 | 3.41 | 85.11 | 4.02 | 0.314 |
| 60 | 3.44 | 83.61 | 3.58 | 0.359 |
| 60 | 3.61 | 75.14 | 1.04 | 0.368 |
| 60 | 3.40 | 85.61 | 4.17 | 0.294 |
| 61 | 3.51 | 80.18 | 2.53 | 0.409 |
| 61 | 3.41 | 85.15 | 4.02 | 0.315 |
| 62 | 3.52 | 79.74 | 2.37 | 0.413 |

TABLE 3-continued

ObjectiveFunction1 values calculated using the fitted TotalPercentYield and PercentAggregate polynomial equations.

| Buffer Concentration (mM) | pH | Total Percent Yield (%) | Percent Aggregate (%) | Objective Function 1 |
|---|---|---|---|---|
| 62 | 3.42 | 84.69 | 3.87 | 0.333 |
| 63 | 3.53 | 79.31 | 2.21 | 0.416 |
| 63 | 3.43 | 84.23 | 3.72 | 0.348 |
| 64 | 3.54 | 78.88 | 2.06 | 0.417 |
| 64 | 3.44 | 83.78 | 3.58 | 0.362 |
| 65 | 3.35 | 88.22 | 4.94 | 0.000 |
| 65 | 3.45 | 83.34 | 3.43 | 0.373 |
| 65 | 3.50 | 80.89 | 2.67 | 0.411 |
| 65 | 3.60 | 76.01 | 1.13 | 0.394 |
| 65 | 3.70 | 71.13 | 1.10 | 0.171 |
| 65 | 3.30 | 90.66 | 5.68 | 0.000 |
| 65 | 3.50 | 80.89 | 2.67 | 0.411 |
| 65 | 3.52 | 79.92 | 2.36 | 0.417 |
| 65 | 3.55 | 78.45 | 1.90 | 0.418 |
| 65 | 3.45 | 83.34 | 3.43 | 0.373 |
| 66 | 3.53 | 79.49 | 2.22 | 0.420 |
| 66 | 3.56 | 78.03 | 1.75 | 0.417 |
| 66 | 3.46 | 82.89 | 3.30 | 0.383 |
| 67 | 3.55 | 78.58 | 1.92 | 0.420 |
| 67 | 3.52 | 80.04 | 2.38 | 0.418 |
| 67 | 3.54 | 79.07 | 2.07 | 0.421 |
| 67 | 3.47 | 82.46 | 3.16 | 0.391 |
| 68 | 3.53 | 79.61 | 2.24 | 0.420 |
| 68 | 3.52 | 80.09 | 2.40 | 0.418 |
| 68 | 3.48 | 82.02 | 3.02 | 0.398 |
| 69 | 3.49 | 81.59 | 2.89 | 0.404 |
| 70 | 3.35 | 88.34 | 5.09 | 0.000 |
| 70 | 3.45 | 83.56 | 3.55 | 0.362 |
| 70 | 3.55 | 78.78 | 1.97 | 0.421 |
| 70 | 3.50 | 81.17 | 2.76 | 0.408 |
| 70 | 3.30 | 90.73 | 5.86 | 0.000 |
| 70 | 3.70 | 71.61 | 1.00 | 0.207 |
| 71 | 3.53 | 79.80 | 2.32 | 0.419 |
| 75 | 3.35 | 88.45 | 5.36 | 0.000 |
| 75 | 3.45 | 83.78 | 3.77 | 0.336 |
| 75 | 3.50 | 81.44 | 2.96 | 0.394 |
| 75 | 3.60 | 76.77 | 1.33 | 0.407 |
| 75 | 3.62 | 75.83 | 1.00 | 0.394 |
| 75 | 3.30 | 90.79 | 6.14 | 0.000 |
| 80 | 3.35 | 88.57 | 5.74 | 0.000 |
| 80 | 3.45 | 84.00 | 4.10 | 0.289 |
| 80 | 3.55 | 79.43 | 2.44 | 0.401 |
| 80 | 3.30 | 90.85 | 6.54 | 0.000 |
| 80 | 3.70 | 72.57 | 1.00 | 0.262 |
| 80 | 3.65 | 74.86 | 1.00 | 0.360 |
| 80 | 3.45 | 84.00 | 4.10 | 0.289 |
| 82 | 3.46 | 83.63 | 4.10 | 0.286 |
| 84 | 3.47 | 83.28 | 4.11 | 0.280 |
| 85 | 3.55 | 79.75 | 2.85 | 0.374 |
| 85 | 3.50 | 81.99 | 3.70 | 0.322 |
| 85 | 3.30 | 90.92 | 7.05 | 0.000 |
| 85 | 3.65 | 75.29 | 1.11 | 0.370 |
| 85 | 3.61 | 77.07 | 1.81 | 0.388 |
| 86 | 3.62 | 76.71 | 1.72 | 0.383 |
| 86 | 3.48 | 82.93 | 4.14 | 0.272 |
| 87 | 3.63 | 76.34 | 1.64 | 0.377 |
| 88 | 3.64 | 75.99 | 1.56 | 0.370 |
| 88 | 3.49 | 82.59 | 4.18 | 0.262 |
| 89 | 3.65 | 75.63 | 1.48 | 0.363 |
| 89 | 3.50 | 82.20 | 4.12 | 0.268 |
| 90 | 3.35 | 88.80 | 6.82 | 0.000 |
| 90 | 3.45 | 84.44 | 5.10 | 0.000 |
| 90 | 3.55 | 80.08 | 3.36 | 0.332 |
| 90 | 3.60 | 77.90 | 2.48 | 0.365 |
| 90 | 3.55 | 80.08 | 3.36 | 0.332 |
| 90 | 3.30 | 90.98 | 7.67 | 0.000 |
| 90 | 3.70 | 73.54 | 1.00 | 0.307 |
| 90 | 3.66 | 75.28 | 1.41 | 0.356 |
| 90 | 3.51 | 81.82 | 4.06 | 0.272 |
| 90 | 3.45 | 84.44 | 5.10 | 0.000 |
| 91 | 3.67 | 74.94 | 1.33 | 0.347 |
| 92 | 3.66 | 75.46 | 1.62 | 0.350 |
| 92 | 3.52 | 81.50 | 4.13 | 0.259 |
| 92 | 3.46 | 84.10 | 5.18 | 0.000 |
| 93 | 3.65 | 75.98 | 1.92 | 0.350 |
| 94 | 3.64 | 76.49 | 2.22 | 0.347 |
| 94 | 3.53 | 81.19 | 4.21 | 0.243 |
| 94 | 3.47 | 83.76 | 5.28 | 0.000 |
| 95 | 3.63 | 77.00 | 2.53 | 0.339 |
| 96 | 3.62 | 77.50 | 2.85 | 0.328 |
| 96 | 3.54 | 80.89 | 4.30 | 0.225 |
| 96 | 3.48 | 83.43 | 5.38 | 0.000 |
| 97 | 3.61 | 78.00 | 3.17 | 0.313 |
| 98 | 3.55 | 80.60 | 4.41 | 0.204 |
| 98 | 3.49 | 83.12 | 5.50 | 0.000 |
| 100 | 3.35 | 89.03 | 8.35 | 0.000 |
| 100 | 3.45 | 84.88 | 6.55 | 0.000 |
| 100 | 3.55 | 80.73 | 4.72 | 0.142 |
| 100 | 3.56 | 80.31 | 4.53 | 0.179 |
| 100 | 3.50 | 82.81 | 5.64 | 0.000 | calculated using TotalPercentYield and PercentAggregate values generated using the Table 2 data set fitted equations described above. Both Table 2 and Table 3 objective function values were then plotted and used to generated the fitted ObjectiveFunction2 equation. This was done to ensure that no "gaps" existed in the data set used to generated the fitted ObjectiveFunction2 equation which could skew the fitted polynomial equation.

The ObjectiveFunction2 equation reveals that the ObjectiveFunction1 values (z axis) obtained by protein A chromatography can be described mathematically as a function of both elution buffer tris(hydroxymethyl)aminomethane acetate salt concentration (x axis value) and pH (y axis value). The ObjectiveFunction2 function is:

$$\text{ObjectiveFunction2}(x,y) = (3.58 \times 10^{-5})\exp[-0.5(0.00171x^2 - 0.1927xy + 50.515y + 0.4540x - 348.52y + 589.487)]$$

where x = tris(hydroxymethyl)aminomethane acetate salt concentration; mM and y = pH The ObjectiveFunction2 equation has a local maximum of 0.466 at a tris(hydroxymethyl)aminomethane acetate salt concentration of 69.0 mM and a pH of 3.58.

In mathematical optimization problems an "objective function" is an equation that, when solved, reveals the values of variables that permit one to obtain maximal, or optimal, values from the objective function. Here, the ObjectiveFuction2 equation described above was used to identify specific elution buffer salt concentrations (x variable) and pH (y variable) values that permit one to use protein A chromatography to obtain a purified Fc peptide chain sample comprising less then 5% aggregate by mass at a total percent yield of Fc peptide chain greater than 70%. A sample with these characteristics is optimal for the preparation of biopharmaceuticals comprising Fc peptide chains.

For example, protein A chromatography elution buffer salt concentration and pH values that produce an objective function value of 0 (see FIG. 4) cannot be used to produce a purified Fc peptide chain sample with the desired, optimal characteristics. In contrast, protein A chromatography elution buffer salt concentration and pH values that produce an objective function value greater than 0.0 up to the maximum possible objective function value of 1.0 (see ObjectiveFunction1 above) represent the range of possible values that can be used to produce a purified Fc peptide chain sample with the desired, optimal characteristics. The best possible elution buffer salt concentration and pH values are those that produce an objective function value as close to 1.0 as possible. For the ObjectiveFunction2 equation the best possible elution buffer salt concentration and pH values are those that produce an objective function value as close to the local maximum of 0.466 as possible.

The Objectivefunction2 equation above and its graphical representation (FIG. 4) can be used to identify specific protein A chromatography elution buffer salt concentration and pH values, or a range of such values, that are optimal for obtaining a purified Fc peptide chain sample comprising less then 5% aggregate by mass at a total percent yield of Fc peptide chain greater than 70%.

EXAMPLE 5

Validation of Objectivefunction2 Equation for Use in Selecting Optimal Protein a Chromatography Elution Buffer Compositions Specific protein A chromatography buffer salt concentration and pH values identified using either the Objectivefunction2 equation, or its graphical representation, were experimentally confirmed to produce purified Fc peptide chain eluate samples comprising less then 5% aggregate by mass at a total percent yield of Fc peptide chain greater than 70% (Table 5). Specifically, the eluted samples obtained contained 2.93% aggregated Fc peptide chain by mass (i.e. the percent aggregate value was 2.93%) at an total percent yield by mass of Fc peptide chain greater than 84.7% (i.e. the total percent yield value was greater than 84.7%).

Figure 4:
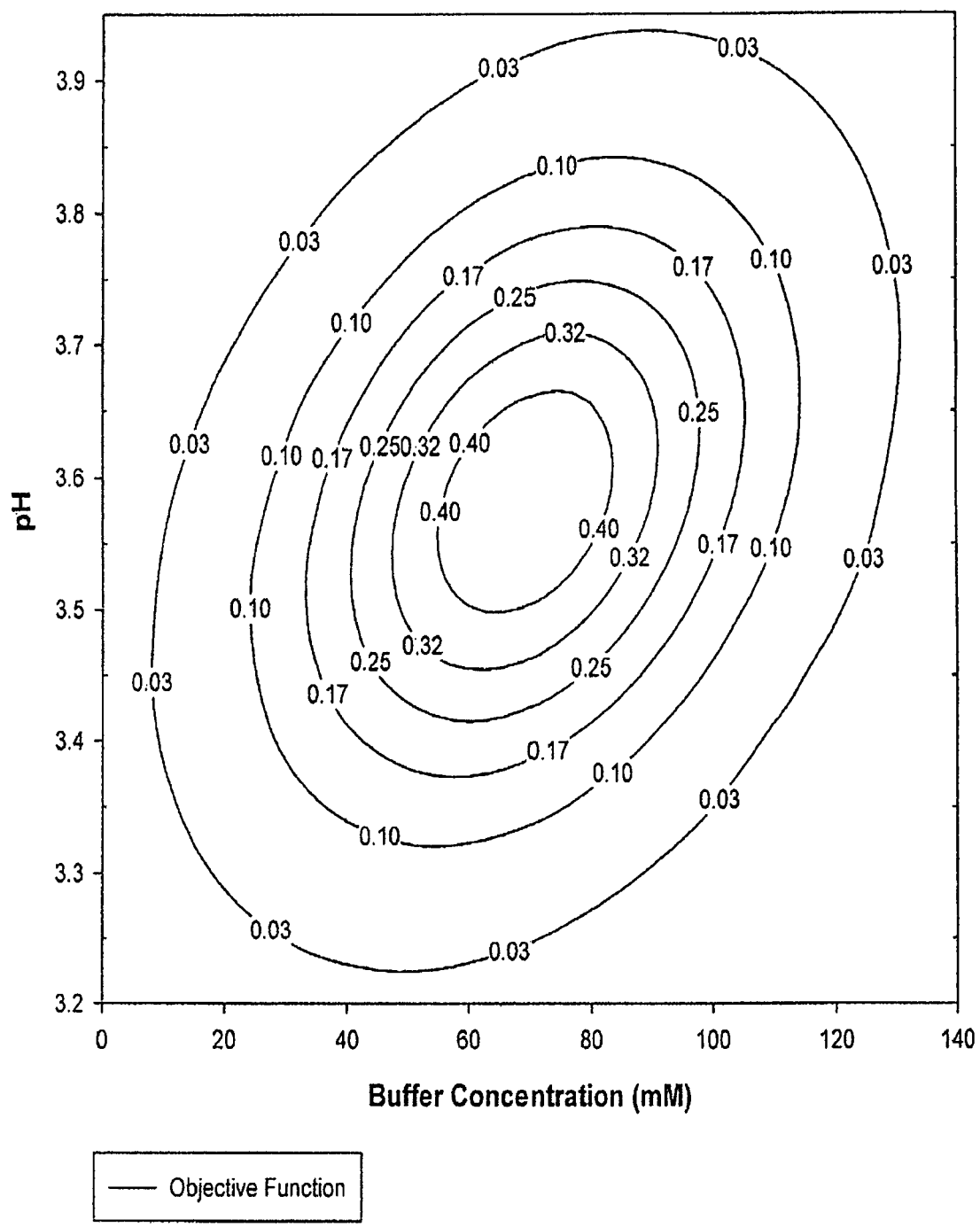
FIG. 4 Plot of the fitted ObjectiveFunction2(x,y) equation. Objective function values are shown as a function of buffer tris(hydroxymethyl)aminomethane acetate salt concentration in mM and pH. Objective function values greater than 0 correspond to protein A chromatography column Fc peptide chain eluate samples comprising less then 5% aggregate by mass at total percent yield values of greater than 70%.

This confirmatory Protein A chromatography experiment was conducted as follows. First, the graphical representation (plot) of the Objectivefunction2 equation was used to identify an ObjectiveFunction2 value greater than 0.4 (z axis) (FIG. 4). The corresponding tris(hydroxymethyl)aminomethane acetate salt concentration (x axis) and pH (y axis) values were then identified. The tris(hydroxymethyl)aminomethane acetate salt concentration value identified was 65 mM. The pH value identified was 3.55.

An aqueous protein A chromatography elution buffer containing 65 mM tris(hydroxymethyl)aminomethane acetate salt at a pH of 3.55 was then prepared. C1374C cell culture, supernatant collection, protein A chromatography column preparation, column equilibration, supernatant loading, and column washes for this confirmatory experiment were performed as described in Example 1 above. Chromatography was performed at a temperature between 19° C. and 25° C. Peptide chains bound to the protein A chromatography column resin were eluted from the protein A chromatography column resin with the elution buffer containing 65 mM tris (hydroxymethyl)aminomethane acetate salt at a pH of 3.55. The protein A chromatography column was then stripped with a solution of 0.1 M tris(hydroxymethyl)aminomethane acetate salt at a pH of 3.0. Protein concentrations, aggregated Fc peptide chain content, and unaggregated Fc peptide chain content in the samples was determined using standard SE-HPLC methods as described in Example 1 above.

Analysis of the eluate samples confirmed that the samples contained 2.93% aggregated Fc peptide chain by mass (i.e. the percent aggregate value was 2.93%) at an total percent yield by mass of Fc peptide chain greater than 84.7% (i.e. the total percent yield was greater than 84.7%). Cell culture supernatants originally loaded onto the protein A chromatography column contained 9.89% aggregate. The overall unaggregated Fc peptide chain specific percent yield from the column after stripping was 91.3% by mass. The PercentAggregate and TotalPercentYield equations were used respectively to predict the percent aggregate values and total percent yield value in eluate samples resulting from protein A chromatography employing an elution buffer comprising 65 mM tris(hydroxymethyl)aminomethane acetate salt (x value) at a pH of 3.55 (y value). The predicted percent aggregate value was 1.7% and the predicted total percent yield value was 78.5%. Both values are reasonably close to the total percent yield and percent aggregate values actually obtained in the eluate sample of this validation experiment.

These results demonstrate that the Objectivefunction2 equation, or its graphical representation, can be used to produce purified Fc peptide chain eluate samples comprising less then 5% aggregate by mass at a total percent yield of Fc peptide chain greater than 70% (Table 5). These results also further confirm that protein A chromatography can be used to separate aggregated Fc peptide chains from unaggregated Fc peptide chains. Results discussed here are representative of four independently conducted validation experiments using two different mimetibody producing cell lines.

The present invention now being fully described, it will be apparent to one of ordinary skill in the art that many changes and modifications can be made thereto without departing from the spirit or scope of the appended claims.

The invention claimed is:

1. A method for producing a solution of purified unaggregated Fc peptide chains comprising the steps of:

a) providing an aqueous sample comprising unaggregated Fc peptide chains and aggregated Fc peptide chains;

b) contacting the sample with a population of protein A peptide chains bound to an insoluble material and capable of binding greater than 70% of the total mass of unaggregated Fc peptide chains and aggregated Fc peptide chains in the sample;

c) contacting the population of protein A peptide chains with an aqueous solution having a salt concentration consisting of tris(hydroxymethyl)aminomethane acetate of 41 mM to 97 mM and a pH of 3.42 to 3.74; and d) removing the aqueous solution from contact with the population of protein A peptide chains to produce a solution of purified unaggregated Fc peptide chains comprising less then 5% aggregated Fc peptide chains;

wherein the total percent yield of Fc peptide chains is greater than 70%.

2. The method of claim 1 wherein the population of protein A peptide chains bound to an insoluble material has a height equivalent to a theoretical plate value of 0.005 cm to 0.05 cm.

3. The method of claim 1 wherein the unaggregated Fc peptide chain is a mimetibody.

4. A method for producing a solution of purified unaggregated Fc peptide chains comprising the steps of:

a) providing an aqueous sample comprising unaggregated Fc peptide chains and aggregated Fc peptide chains;

b) contacting the sample with a population of protein A peptide chains bound to an insoluble material and capable of binding greater than 70% of the total mass of unaggregated Fc peptide chains and aggregated Fc peptide chains in the sample;

c) contacting the population of protein A peptide chains with an aqueous solution having a salt concentration consisting of tris(hydroxymethyl)aminomethane acetate of 55 mM to 85 mM and a pH of 3.50 to 3.66; and d) removing the aqueous solution from contact with the population of protein A peptide chains to produce a solution of purified unaggregated Fc peptide chains comprising less then 5% aggregated Fc peptide chains;

wherein the total percent yield of Fc peptide chains is greater than 70%.

5. The method of claim 4 wherein the population of protein A peptide chains bound to an insoluble material has a height equivalent to a theoretical plate value of 0.005 cm to 0.05 cm.

6. The method of claim 4 wherein the unaggregated Fc peptide chain is a mimetibody.

7. A method for producing a solution of purified unaggregated mimetibody Fc peptide chains comprising the steps of:
   a) providing an aqueous sample comprising unaggregated mimetibody Fc peptide chains and aggregated mimetibody Fc peptide chains;
   b) contacting the sample with a population of protein A peptide chains bound to an insoluble material and capable of binding greater than 70% of the total mass of unaggregated mimetibody Fc peptide chains and aggregated mimetibody Fc peptide chains in the sample;
   c) contacting the population of protein A peptide chains with an aqueous solution having a salt concentration consisting of tris (hydroxymethyl) aminomethane acetate of 55 mM to 85 mM and a pH of 3.50 to 3.66; and
   d) removing the aqueous solution from contact with the population of protein A peptide chains to produce a solution of purified unaggregated mimetibody Fc peptide chains comprising less then 5% aggregated mimetibody Fc peptide chains;
   wherein the total percent yield of mimetibody Fc peptide chains is greater than 70%.

8. The method of claim 7 wherein the population of protein A peptide chains bound to an insoluble material has a height equivalent to a theoretical plate value of 0.005 cm to 0.05 cm.

* * * * *

SEQUENCE LISTING

<160> NUMBER OF SEQ ID NOS: 7

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
 1               5                  10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys

```
                 35                  40                  45

Leu Asn Asp Ser Gln Ala Pro Lys
         50                  55

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
 1               5                  10                  15

Tyr Glu Ile Leu Asn Met Pro Asn Leu Asn Glu Glu Gln Arg Asn Gly
             20                  25                  30

Phe Ile Gln Ser Leu Lys Asp Asp Pro Ser Gln Ser Thr Asn Val Leu
         35                  40                  45

Gly Glu Ala Lys Lys Leu Asn Glu Ser Gln Ala Pro Lys
     50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
 1               5                  10                  15

Leu Asn Met Pro Asn Leu Asn Glu Glu Gln Arg Asn Gly Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Glu Ser Gln Ala Pro Lys
     50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Gly Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Gly Phe Ile Gln
             20                  25                  30
```

Ser Leu Lys Asp Asp Pro Ser Val Ser Lys Glu Ile Leu Ala Glu Ala
        35                  40                  45

Lys Lys Leu Asn Asp Ala Gln Ala Pro Lys
 50                  55

<210> SEQ ID NO 6
<211> LENGTH: 291
<212> TYPE: PRT
<213> ORGANISM: Staphylococcus aureus

<400> SEQUENCE: 6

Ala Gln His Asp Glu Ala Gln Gln Asn Ala Phe Tyr Gln Val Leu Asn
 1               5                  10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Lys Phe
 50                  55                  60

Asn Lys Asp Gln Gln Ser Ala Phe Tyr Glu Ile Leu Asn Met Pro Asn
65                  70                  75                  80

Leu Asn Glu Glu Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Gln Gln Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ala Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 7
<211> LENGTH: 247
<212> TYPE: PRT
<213> ORGANISM: Artificial Sequence
<220> FEATURE:
<223> OTHER INFORMATION: An erythropoietin mimetibody amino acid
      sequence derived from Homo sapiens IgG1 antibody sequences and -continued

```
      bioactive erythropoietin mimicking peptide chains.

<400> SEQUENCE: 7

Gln Ile Gln Gly Gly Thr Tyr Ser Cys His Phe Gly Pro Leu Thr Trp
 1               5                  10                  15

Val Cys Lys Pro Gln Gly Gly Gly Ser Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
    50                  55                  60

Asp Val Ser Gln Glu Asp Pro Glu Val Gln Phe Asn Trp Tyr Val Asp
65                  70                  75                  80

Gly Val Glu Val His Asn Ala Lys Thr Lys Pro Arg Glu Glu Gln Phe
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Gly Leu
        115                 120                 125

Pro Ser Ser Ile Glu Lys Thr Ile Ser Lys Ala Lys Gly Gln Pro Arg
    130                 135                 140

Glu Pro Gln Val Tyr Thr Leu Pro Pro Ser Gln Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Arg Leu Thr Val Asp Lys Ser Arg Trp Gln Glu Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Leu Gly Lys
                245
```